(12) United States Patent
Xiong et al.

(10) Patent No.: US 8,778,278 B2
(45) Date of Patent: Jul. 15, 2014

(54) NON BIO-ADHESIVE POLYMER COATING COMPOSITION, ARTICLES AND DEVICES THEREOF

(75) Inventors: Mingna Xiong, Shanghai (CN); Bing Zhang, Shanghai (CN); Liping Zheng, Shanghai (CN); Hui Lei, Shanghai (CN); Su Lu, Shanghai (CN); Liming Yu, Clifton Park, NY (US); Lin Chen, Shanghai (CN); Wenqing Peng, Shanghai (CN); Yanrong Zhu, Shanghai (CN)

(73) Assignee: General Electric Company, Niskayuna, NY (US)

( * ) Notice: Subject to any disclaimer, the term of this patent is extended or adjusted under 35 U.S.C. 154(b) by 1340 days.

(21) Appl. No.: 12/503,581

(22) Filed: Jul. 15, 2009

(65) Prior Publication Data

US 2011/0015099 A1 Jan. 20, 2011

(51) Int. Cl.
*B01L 3/00* (2006.01)

(52) U.S. Cl.
USPC ............ 422/500; 422/551; 525/474; 525/477

(58) Field of Classification Search
USPC ........... 525/474, 477, 478, 479; 422/500, 551
See application file for complete search history.

(56) References Cited

U.S. PATENT DOCUMENTS

| | | | |
|---|---|---|---|
| 5,480,946 A * | 1/1996 | Mueller et al. ................ | 525/479 |
| 7,217,754 B2 | 5/2007 | Koloski et al. | |
| 7,344,783 B2 | 3/2008 | Shea | |
| 7,407,709 B2 | 8/2008 | Zhou et al. | |
| 2003/0065101 A1 * | 4/2003 | Blakeney et al. ............. | 525/288 |
| 2004/0019143 A1 | 1/2004 | Koloski et al. | |
| 2005/0136266 A1 | 6/2005 | Zhou et al. | |
| 2007/0048349 A1 | 3/2007 | Salamone et al. | |
| 2009/0098176 A1 | 4/2009 | Helmus et al. | |

FOREIGN PATENT DOCUMENTS

WO 03015748 A2 2/2003

OTHER PUBLICATIONS

David Castel, Amandine Pitaval, Marie-Anne Debily and Xavier Gidrol; "Cell microarrays in drug discovery"; CEA, DSV, DRR, Service de Ge'nomique Fonctionnelle, 2 rue Gaston Cre'mieux—CP 22, 91057 Evry Cedex, France; www.drugdiscoverytoday.com; 7Pages.

Salman R Khetani and Sangeeta N Bhatia; "Engineering tissues for in vitro applications"; www.sciencedirect.com; Current Opinion in Biotechnology 2006, 17:524-531.

Young-Yeon Ji , Yong-Cheol Hong, Suck-Hyun Lee, Sung-Dae Kim and Sang-Sik Kim; "Formation of super-hydrophobic and water-repellency surface with hexamethyldisiloxane (HMDSO) coating on polyethyleneteraphtalate fiber by atmosperic pressure plasma polymerization"; 0257-8972/$—see front matter © 2008 Published by Elsevier B.V. doi:10.1016/j.surfcoat.2008.06.151; 5Pages.

(Continued)

*Primary Examiner* — Jill Warden
*Assistant Examiner* — Dwayne K Handy
(74) *Attorney, Agent, or Firm* — Jenifer E. Haeckl

(57) ABSTRACT

The invention is a device comprising a substrate and a material provided on at least a portion of the substrate and having an exposed surface. The exposed surface of the material is non bio-adhesive. The invention further includes a non bio-adhesive material composition and a method of making a device having the same non bio-adhesive surface. The invention further provides a device having a coating of a hydrophobic material. In particular, the hydrophobic material coated portion of the device is resistant to bio-adhesion.

12 Claims, 5 Drawing Sheets

TRIS-polymer coated glass slide

(56) References Cited

OTHER PUBLICATIONS

Andrew L. Hook, Helmut Thissen, Jason P. Hayes and Nicolas H. Voelcker; "Spatially controlled electro-stimulated DNA adsorption and desorption for biochip applications"; Received Jul. 20, 2005; received in revised form Oct. 4, 2005; accepted Oct. 12, 2005; 9Pages.

Didier Falconnet, Gabor Csucs, H. Michelle Grandin and Marcus Textor; "Surface engineering approaches to micropattern surfaces for cell-based assays"; Received Oct. 17, 2005; accepted Dec. 30, 2005; 20Pages.

* cited by examiner

Uncoated glass slide

TRIS-polymer coated glass slide

NON BIO-ADHESIVE POLYMER COATING COMPOSITION, ARTICLES AND DEVICES THEREOF

BACKGROUND

This invention relates generally to polymer-based coatings and more particularly to non bio-adhesive polymer-based coatings.

The aim of applying coatings is to improve surface properties of an object. Coatings can affect physical properties of various materials depending upon the chemical composition of the coating materials. Such properties include, but are not limited to, adhesion, corrosiveness, scratch resistance, wash resistance, waterproof, and color proof. Advances in coating chemistry have increased the quality, specificity (such as hydrophobicity) and compatibility of coatings with various objects and their use in various applications. For example, silicone resins are used for durable hydrophobic surface coatings. In another example, surface modification of polyester fibers is carried out by plasma polymerization coating technique using hexamethyldisiloxane to form a high water-repellency and super-hydrophobic coating.

Antibacterial coatings for medical devices have long been needed in biomedical and biological applications. For example, antibacterial coatings are used in connection with cell and tissue culture applications, in devices for cell based and protein based assays, in medical devices such as injectable cell delivery vehicles, in CT or MR machines, in surgical devices, in devices for immunoisolation-based therapies and in other in vitro or in vivo usages.

Cell-based assays have become an integral part of drug screening in the pharmaceutical industry. These assays are useful in evaluating potential drug targets by functionally characterizing the effects of drugs on cells, and in assessing specificity and efficacy of drug leads to identify potential targets for drugs and also to determine the mechanism of action of that drug to identify its target. There is an increasing need for high throughput cell-based assays in the functional exploration of genomes and also for analyzing phenotypes associated with genome functionality. Cell microarrays provide an attractive solution while providing a slide for at least 5000-6000 spots, which enables a genome-wide screen on only a few slides. Therefore, cell microarray would increase the throughput significantly, while at the same time minimizing the use of expensive reagents and scarce biological samples such as rare cells. However, adherent cells have a tendency to expand over the available surrounding surface and cause cross contamination over other neighboring spots. Therefore, to spot cells in high-density cell growth on slides or plates is becoming a challenge for biologists. A successful mechanism for the prevention of cross-contamination of cells and DNA between adjacent colonies or DNA spots has not yet been successfully implemented. A non bio-adhesive coating on slides may help to maintain cells on one particular spot and render high-density cell array feasible. Therefore, an emerging need in various areas of biology and medicine is the development of cell culture support, equipment for cell-based assays and cell microarrays and devices for medical purposes, that are resistant to contamination. Therefore, it would be highly desirable to develop a biocompatible non bio-adhesive coating for use in such applications.

BRIEF DESCRIPTION

The compositions, devices and methods of the invention generally relate to novel polymer materials and coatings that are non bio-adhesive and are strongly resistant to cellular and microbial adhesion. These materials and coatings are a much-needed solution for preventing cellular contamination while still providing the added benefit of biocompatibility for cell-based assays and medical devices.

In one embodiment, a device having a non bio-adhesive coating is provided. The device comprises a substrate; and a material comprising a plurality of structure (I) groups provided on at least a portion of the substrate:

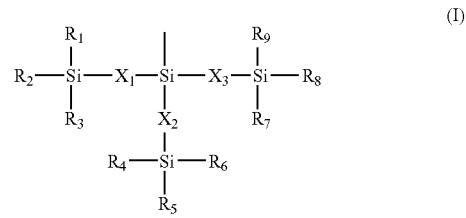

wherein $R_1$, $R_2$, $R_3$, $R_4$, $R_5$, $R_6$, $R_7$, $R_8$ and $R_9$ are independently at each occurance a C1-C10 aliphatic radical, a C3-C20 cycloaliphatic radical, or C6-C20 aromatic radical; and $X_1$, $X_2$, $X_3$ are independently at each occurance a sulphur, nitrogen, oxygen, or carbon. The material is provided on at least a portion of the substrate, and has an exposed surface that is non-bioadhesive.

In another embodiment, a non bio-adhesive copolymer composition is provided. The copolymer comprises at least one structure (I) group, at least one cross linker comprising a derivative of a acrylate, and at least one monomer of a acrylate or its derivative. The Structure (I) groups represent,

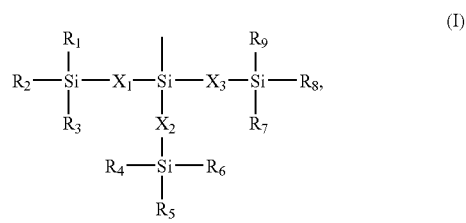

wherein $R_1$, $R_2$, $R_3$, $R_4$, $R_5$, $R_6$, $R_7$, $R_8$ and $R_9$ are independently at each occurance a C1-C10 aliphatic radical, a C3-C20 cycloaliphatic radical, or C6-C20 aromatic radical; and $X_1$, $X_2$, $X_3$ are independently at each occurance a sulphur, nitrogen, oxygen, or carbon.

In yet another embodiment, a method of making a device having a non bio-adhesive surface is provided. The method comprises a step of applying a material onto the surface of the device comprises a plurality of structure (I) groups.

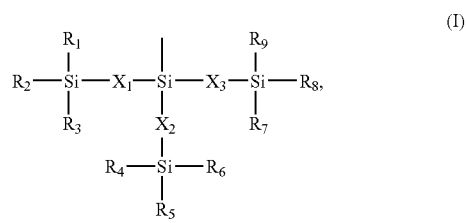

wherein $R_1$, $R_2$, $R_3$, $R_4$, $R_5$, $R_6$, $R_7$, $R_8$ and $R_9$ are independently at each occurance a C1-C10 aliphatic radical, a C3-C20 cycloaliphatic radical, or C6-C20 aromatic radical; and $X_1, X_2, X_3$ are independently at each occurance a sulphur, nitrogen, oxygen, or carbon.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1A:
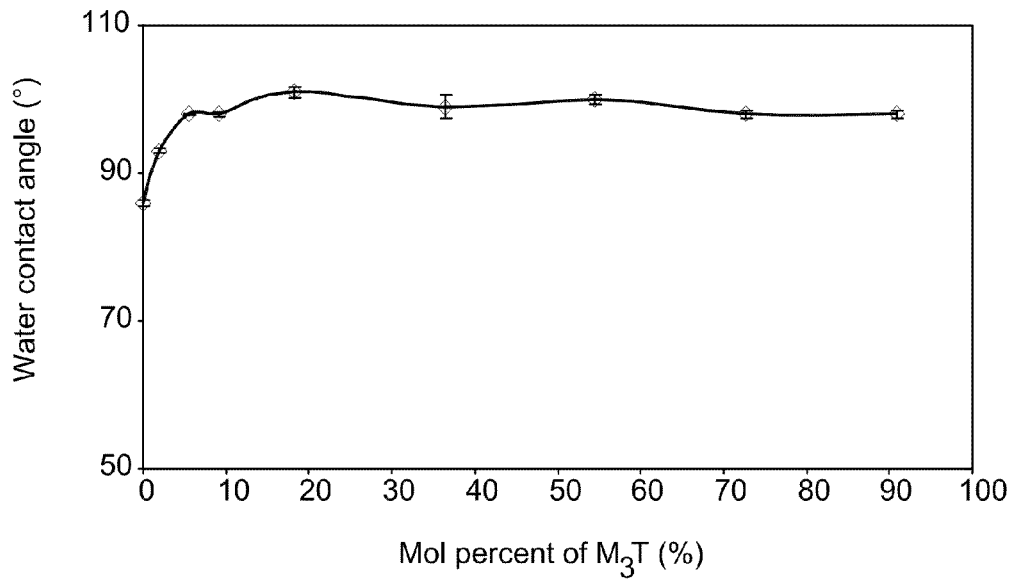
FIG. 1A is a graph showing the dependence of water contact angle with mole percent of $M_3T$.

To more clearly and concisely describe and point out the subject matter of the claimed invention, the following definitions are provided for specific terms, which are used in the following description and the appended claims. Throughout the specification, exemplification of specific terms should be considered as non-limiting examples.

The invention relates to a device comprising a substrate with a material provided on at least a portion of the substrate and having an exposed surface. The exposed surface of the material is non bio-adhesive. The invention further includes a non bio-adhesive material composition and a method of making a device having the same non bio-adhesive surface. In one embodiment, the invention provides a device having a coating of a hydrophobic material. In particular, the hydrophobic material coated portion of the device is resistant to bio-adhesion.

A "substrate", as referred to herein, is a base or a holder, which provides support for forming a coating on it. A coated substrate may be a micro array plate, a culture flask or a plate for culturing cells, a cell based assay system, a membrane, a vessel, a tank or a portion of a medical device. The coated substrate can be an inner wall or an outer wall of a medical device. For example, the substrate may be an inner and/or outer wall of a catheter, an injection needle, an operation table, or any equipment related to medical purposes. The coated substrate may be an inner wall of a tank. For example, the tank may be a water tank, a tank for storing any food or beverage, or a tank for keeping any biological species. In some embodiments, the "substrate" may be a tray or a plate for holding or supporting a patient body or part of a patient body in a medical device such as an X-ray system, a magnetic resonance system, a computed tomography system, an ultrasound system, a Radiography (RAD), Radiography and Fluoroscopy (R & F), or a Mammography machine, wherein the substrate is coated by the material of the present invention. In other embodiments, the substrate may be a probe for ultra sound or positron emission tomography (PET) imaging machines for use in human body imaging, wherein the probe is coated with embodiments of the material of the present invention. The coating may also be used on surgery tables to prevent contamination that may cause infection in a patient.

The term "exposed surface" as referred to herein, is a surface of a coated substrate, which is exposed to external agents or environment.

The term "non bio-adhesive" as referred to herein, is a material or an article, which is resistant to adhesion by biological molecules. The term 'non' represents here 'very low' but not an absolute value. Non-limiting examples of biological molecules are protein, DNA, RNA, cells, tissues, and viruses.

The term "material" as referred to herein, is a substance provided on the surface of the device may comprise small molecules, oligomers, polymers, organic-inorganic hybrids or mixtures thereof.

The term "aliphatic radical" as referred to herein, is an organic radical having a valence of at least one consisting of a linear or branched array of atoms which is not cyclic. Aliphatic radicals are defined to comprise at least one carbon atom. The array of atoms comprising the aliphatic radical may include heteroatoms such as nitrogen, sulfur, silicon, selenium and oxygen or may be composed exclusively of carbon and hydrogen. For convenience, the term "aliphatic radical" is defined herein to encompass, as part of the "linear or branched array of atoms which is not cyclic" a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylpent-1-yl radical is a $C_6$ aliphatic radical comprising a methyl group, the methyl group being a functional group which is an alkyl group. Similarly, the 4-nitrobut-1-yl group is a $C_4$ aliphatic radical comprising a nitro group, the nitro group being a functional group. An aliphatic radical may be a haloalkyl group which comprises one or more halogen atoms which may be the same or different. Halogen atoms include, for example; fluorine, chlorine, bromine, and iodine. Aliphatic radicals comprising one or more halogen atoms include the alkyl halides trifluoromethyl, bromodifluoromethyl, chlorodifluoromethyl, hexafluoroisopropylidene, chloromethyl, difluorovinylidene, trichloromethyl, bromodichloromethyl, bromoethyl, 2-bromotrimethylene (e.g., —$CH_2CHBrCH_2$—), and the like. Further examples of aliphatic radicals include allyl, aminocarbonyl (i.e., —$CONH_2$), carbonyl, 2,2-dicyanoisopropylidene (i.e., —$CH_2C(CN)_2CH_2$—), methyl (i.e., —$CH_3$), methylene (i.e., —$CH_2$—), ethyl, ethylene, formyl (i.e., —CHO), hexyl, hexamethylene, hydroxymethyl (i.e., —$CH_2OH$), mercaptomethyl (i.e., —$CH_2SH$), methylthio (i.e., —$SCH_3$), methylthiomethyl (i.e., —$CH_2SCH_3$), methoxy, methoxycarbonyl (i.e., $CH_3OCO$—), nitromethyl (i.e., —$CH_2NO_2$), thiocarbonyl, trimethylsilyl (i.e., $(CH_3)_3Si$—), t-butyldimethylsilyl, 3-trimethyoxysilylpropyl (i.e., $(CH_3O)_3SiCH_2CH_2CH_2$—), vinyl, vinylidene, and the like. By way of further example, a $C_1$-C10 aliphatic radical contains at least one but no more than 10 carbon atoms. A methyl group (i.e., $CH_3$—) is an example of a $C_1$ aliphatic radical. A decyl group (i.e., $CH_3$ $(CH_2)_9$—) is an example of a $C_{10}$ aliphatic radical.

The term "cycloaliphatic radical" as referred to herein, is a radical having a valence of at least one, and comprising an array of atoms which is cyclic but which is not aromatic. As defined herein a "cycloaliphatic radical" does not contain an aromatic group. A "cycloaliphatic radical" may comprise one or more noncyclic components. For example, a cyclohexylmethyl group ($C_6H_{11}CH_2$—) is a cycloaliphatic radical which comprises a cyclohexyl ring (the array of atoms which is cyclic but which is not aromatic) and a methylene group (the noncyclic component). The cycloaliphatic radical may include heteroatoms such as nitrogen, sulfur, selenium, silicon and oxygen, or may be composed exclusively of carbon and hydrogen. For convenience, the term "cycloaliphatic radical" is defined herein to encompass a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylcyclopent-1-yl radical is a $C_6$ cycloaliphatic radical comprising a methyl group, the methyl group being a functional group which is an alkyl group. Similarly, the 2-nitrocyclobut-1-yl radical is a $C_4$ cycloaliphatic radical comprising a nitro group, the nitro group being a functional group. A cycloaliphatic radical may comprise one or more halogen atoms, which may be the same or different. Halogen atoms include, for example; fluorine, chlorine, bromine, and iodine. Cycloaliphatic radicals comprising one or more halogen atoms include 2-trifluoromethylcyclohex-1-yl, 4-bromodifluoromethylcyclooct-1-yl, 2-chlorodifluoromethylcyclohex-1-yl, hexafluoroisopropylidene-2,2-bis(cyclohex-4-yl) (i.e., —$C_6H_{10}C(CF_3)_2$ $C_6H_{10}$—), 2-chloromethylcyclohex-1-yl, 3-difluoromethylenecyclohex-1-yl, 4-trichloromethylcyclohex-1-yloxy, 4-bromodichloromethylcyclohex-1-ylthio, 2-bromoethylcyclopent-1-yl, 2-bromopropylcyclohex-1-yloxy (e.g., $CH_3CHBrCH_2C_6H_{10}O$—), and the like. Further examples of cycloaliphatic radicals include 4-allyloxycyclohex-1-yl, 4-aminocyclohex-1-yl (i.e., $H_2NC_6H_{10}$—), 4-aminocarbonylcyclopent-1-yl (i.e., $NH_2COC_5H_8$—), 4-acetyloxycyclohex-1-yl, 2,2-dicyanoisopropylidenebis(cyclohex-4-yloxy) (i.e., —$OC_6H_{10}C(CN)_2C_6H_{10}O$—), 3-methylcyclohex-1-yl, methylenebis(cyclohex-4-yloxy) (i.e., —$OC_6H_{10}CH_2C_6H_{10}O$—), 1-ethylcyclobut-1-yl, cyclopropylethenyl, 3-formyl-2-terahydrofuranyl, 2-hexyl-5-tetrahydrofuranyl, hexamethylene-1,6-bis(cyclohex-4-yloxy) (i.e., —$OC_6H_{10}(CH_2)_6C_6H_{10}O$—), 4-hydroxymethylcyclohex-1-yl (i.e., 4-$HOCH_2C_6H_{10}$—), 4-mercaptomethylcyclohex-1-yl (i.e., 4-$HSCH_2C_6H_{10}$—), 4-methylthiocyclohex-1-yl (i.e., 4-$CH_3SC_6H_{10}$—), 4-methoxycyclohex-1-yl, 2-methoxycarbonylcyclohex-1-yloxy (2-$CH_3OCOC_6H_{10}O$—), 4-nitromethylcyclohex-1-yl (i.e., $NO_2CH_2C_6H_{10}$—), 3-trimethylsilylcyclohex-1-yl, 2-t-butyldimethylsilylcyclopent-1-yl, 4-trimethoxysilylethylcyclohex-1-yl (e.g., $(CH_3O)_3$ $SiCH_2CH_2C_6H_{10}$—), 4-vinylcyclohexen-1-yl, vinylidenebis (cyclohexyl), and the like. The term "a $C_3$-$C_{10}$ cycloaliphatic radical" includes cycloaliphatic radicals containing at least three but no more than 10 carbon atoms. The cycloaliphatic radical 2-tetrahydrofuranyl ($C_4H_7O$—) represents a $C_4$ cycloaliphatic radical. The cyclohexylmethyl radical ($C_6H_{11}CH_2$—) represents a $C_7$ cycloaliphatic radical.

The term "aromatic radical" as referred to herein, is an array of atoms having a valence of at least one comprising at least one aromatic group. The array of atoms having a valence of at least one comprising at least one aromatic group may include heteroatoms such as nitrogen, sulfur, selenium, silicon and oxygen, or may be composed exclusively of carbon and hydrogen. As used herein, the term "aromatic radical" includes but is not limited to phenyl, pyridyl, furanyl, thienyl, naphthyl, phenylene, and biphenyl radicals. As noted, the aromatic radical contains at least one aromatic group. The aromatic group is invariably a cyclic structure having 4n+2 "delocalized" electrons where "n" is an integer equal to 1 or greater, as illustrated by phenyl groups (n=1), thienyl groups (n=1), furanyl groups (n=1), naphthyl groups (n=2), azulenyl groups (n =2), anthraceneyl groups (n=3) and the like. The aromatic radical may also include nonaromatic components. For example, a benzyl group is an aromatic radical, which comprises a phenyl ring (the aromatic group) and a methylene group (the nonaromatic component). Similarly a tetrahydronaphthyl radical is an aromatic radical comprising an aromatic group ($C_6H_3$) fused to a nonaromatic component —$(CH_2)_4$—. For convenience, the term "aromatic radical" is defined herein to encompass a wide range of functional groups such as alkyl groups, alkenyl groups, alkynyl groups, haloalkyl groups, haloaromatic groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylphenyl radical is a $C_7$ aromatic radical comprising a methyl group, the methyl group being a functional group which is an alkyl group. Similarly, the 2-nitrophenyl group is a $C_6$ aromatic radical comprising a nitro group, the nitro group being a functional group. Aromatic radicals include halogenated aromatic radicals such as 4-trifluoromethylphenyl, hexafluoroisopropylidenebis(4-phen-1-yloxy) (i.e., —$OPhC(CF_3)_2PhO$—), 4-chloromethylphen-1-yl, 3-trifluorovinyl-2-thienyl, 3-trichloromethylphen-1-yl (i.e., 3-$CCl_3Ph$-), 4-(3-bromoprop-1-yl)phen-1-yl (i.e., 4-$BrCH_2CH_2CH_2Ph$-), and the like. Further examples of aromatic radicals include 4-allyloxyphen-1-oxy, 4-aminophen-1-yl (i.e., 4-$H_2NPh$-), 3-aminocarbonylphen-1-yl (i.e., $NH_2COPh$-), 4-benzoylphen-1-yl, dicyanomethylidenebis (4-phen-1-yloxy) (i.e., —$OPhC(CN)_2PhO$—), 3-methylphen-1-yl, methylenebis(4-phen-1-yloxy) (i.e., —$OPhCH_2PhO$—),3methylphen-1yl, methylbis(4-phen-1yloxy) (i.e., —$OPhCH_2PhO$—), 2-ethylphen-1-yl, phenylethenyl, 3-formyl-2-thienyl, 2-hexyl-5-furanyl, hexamethylene-1,6-bis(4-phen-1-yloxy) (i.e., —$OPh(CH_2)_6$ PhO—), 4-hydroxymethylphen-1-yl (i.e., 4-$HOCH_2Ph$-), 4-mercaptomethylphen-1-yl (i.e., 4-$HSCH_2Ph$-), 4-methylthiophen-1-yl (i.e., 4-$CH_3SPh$-), 3-methoxyphen-1-yl, 2-methoxycarbonylphen-1-yloxy (e.g., methyl salicyl), 2-nitromethylphen-1-yl (i.e., 2-$NO_2CH_2Ph$), 3-trimethylsilylphen-1-yl, 4-t-butyldimethylsilylphenl-1-yl, 4-vinylphen-1-yl, vinylidenebis(phenyl), and the like. The term "a $C_3$-$C_{10}$ aromatic radical" includes aromatic radicals containing at least three but no more than 10 carbon atoms. The aromatic radical 1-imidazolyl ($C_3H_2N_2$—) represents a $C_3$ aromatic radical. The benzyl radical ($C_7H_7$—) represents a $C_7$ aromatic radical.

The term "organic-inorganic hybrid" as referred to herein, is a material with or without having interactions between the inorganic and organic units. These materials are used for various systems, such as highly crystalline ordered coordination polymers or amorphous sol-gel compounds.

One embodiment of the device of this invention comprises a substrate; a material comprising a plurality of structure (I) groups provided on at least a portion of the substrate.

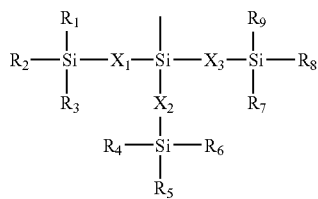
(I)

wherein $R_1$, $R_2$, $R_3$, $R_4$, $R_5$, $R_6$, $R_7$, $R_8$ and $R_9$ are independently at each occurance a C1-C10 aliphatic radical, a C3-C20 cycloaliphatic radical, or C6-C20 aromatic radical; and $X_1$, $X_2$, $X_3$ are independently at each occurance a sulphur, nitrogen, oxygen, or carbon. The portion of the substrate may be an exposed surface. The exposed surface of the material is non bio-adhesive.

Some embodiments describe $R_1$ to $R_{10}$ groups as independent 'lower lakyl' groups. The term "lower alkyl" means an alkyl group having 1 to 10 carbon atoms. Examples of lower alkyl groups include, but not limited to, methyl, ethyl, propyl, butyl, or isopropyl groups. The phenyl group may have substituted side chains with carbon atoms not more than 4. The phenyl groups may also have substituted side chains with heteroatoms, such as sulfur, oxygen, nitrogen, or any halogen. $X_1$, $X_2$ and $X_3$ independently denote heteroatoms such as oxygen, sulfur, carbon or nitrogen. In some embodiments, the structure (I) may be a hydrophobic monomer. In one embodiment, structure (I) comprises a Tris(trimethylsiloxy)silyl (TRIS) group.

In one embodiment, the material provided on the substrate comprises small molecules, such as for example, silanes. Non-limiting examples of one or more small molecules are 3-[tris(trimethyl)siloxysilyl]propyl methacrylate, tris(trimethylsiloxy)(vinyl)silane, tris(trimethylsiloxy)silane, (3-aminopropyl)tris(trimethylsiloxy)silane, 3-(chloropropyl)tris (trimethylsiloxy)silane, tris(trimethylsiloxy)chlorosilane, 3-(acryloxypropyl)Tris(trimethylsiloxy)-silane, phenyl-Tris (trimethylsiloxy)-silane, tris[tris(trimethylsiloxy)siloxy]methylsilane, bis{3-[tris(trimethylsiloxy)silyl] propyl}fumarate, methyltris(trimethylsiloxy)silane, 3-acryloxypropyltris(trimethylsiloxy)silane, 3-methacryloxypropyltris(trimethylsiloxy)silane, p-styryltris(trimethylsiloxy)silane, 2-(5-norbornenyl)ethyltris(trimethylsiloxy)silane, tris(trimethylsiloxy)methoxysilane, tris (trimethylsiloxy)ethoxysilane, tris(trimethylsiloxy)silanol, tris(triethylsiloxy)methoxysilane, tris(triethylsiloxy)ethoxysilane, tris(triethylsiloxy)silanol, allyltris(trimethylsiloxy) silane, allyltris(triethylsiloxy)silane, or mixtures thereof.

In another embodiment, the material comprises oligomers. The oligomer may have the similar composition of a polymer, but consists of a limited number of monomer units compared to the polymer, which at least in principle, consists of a unlimited number of monomers. The oligomer consists of only a few monomer units such as a dimer, trimer; tetramer etc. or a mixture of them. The upper limit of repeating unit in an oligomer is about ten.

In another embodiment, the material comprises polymers. The polymer may be a copolymer such as, but not limited to, block copolymer, random copolymer, alternate copolymer, graft copolymer or a combination thereof.

In yet another embodiment, the material comprises organic-inorganic hybrids. The inorganic material of organic-inorganic hybrid comprises at least one material selected from the group consisting of silica, titania, zinc oxide, alumina, zirconia, vanadia, chromia, ceria, iron oxide, antimony oxide, tin oxide, boron nitride, aluminosilicates, talc, graphite, carbon black, hydrolyzed graphite, and mixtures thereof. In some embodiments, the material has a diameter in a range from about 0.1 nm to about 1 mm.

In one embodiment, the non bio-adhesive material may be hydrophobic material. Such a hydrophobic material may comprise a hydrophobic group, which is a nonpolar group having less affinity for water (hydrophobic) and repels biological molecules. In a non-limiting example, the copolymer comprises at least one hydrophobic monomer and at least one cross linker. In some embodiments, the hydrophobic monomer comprises a Tris(trimethylsiloxy)silyl (TRIS) group. The hydrophobic monomer, in one example, is Tris(trimethylsiloxy)silyl methacrylate ($M_3T$).

In one embodiment, the invention provides a functionalized or modified silane containing polymer composition comprising a carbon chain with cross linkers and hydrophobic groups. The carbon chain may include cross linker residues having structures II, III, and IV, wherein $R_{10}$ is a hydrogen atom, a hydroxyl, a halogen or an alkoxy group; $R_{11}$ and $R_{12}$ independently denote a hydrogen atom, a halogen atom, an alkoxy group, a hydroxyl group, an alkyl group or an aryl group.

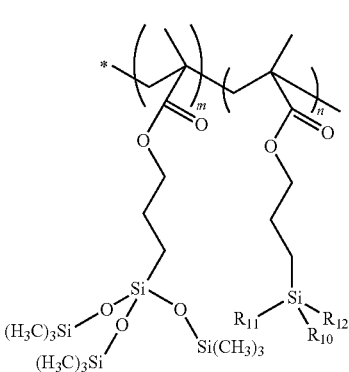
(II)

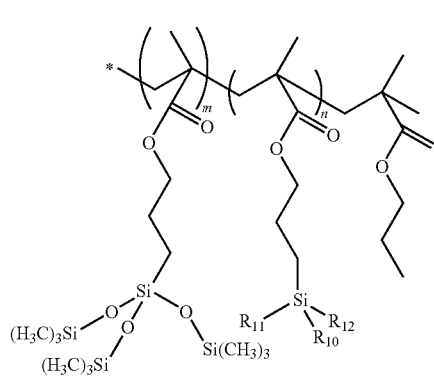
(III)

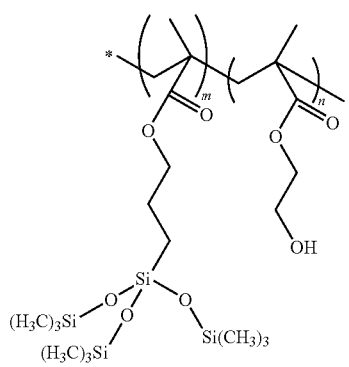

(IV)

Silane containing functional moieties include, but are not limited to, the structures described below.

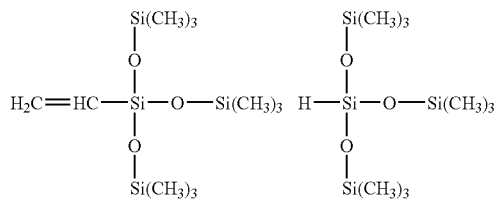

3-[Tris(trimethyl)siloxysilyl]propyl methacrylate

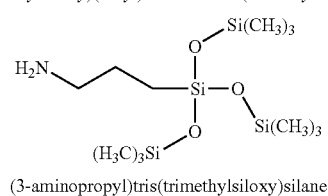

Tris(trimethylsiloxy)(vinyl)silane   Tris(trimethylsiloxy)silane

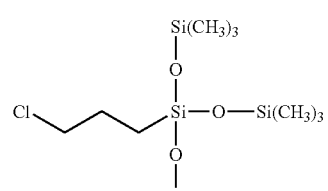

(3-aminopropyl)tris(trimethylsiloxy)silane

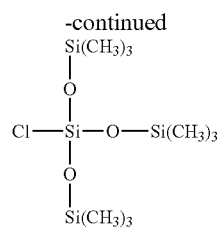

3-(chloropropyl)tris(trimethylsiloxy)silane

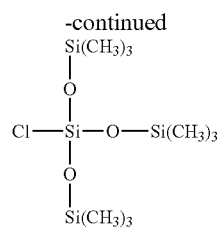

Tris(trimethylsiloxy)chlorosilane

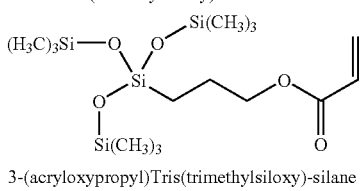

3-(acryloxypropyl)Tris(trimethylsiloxy)-silane

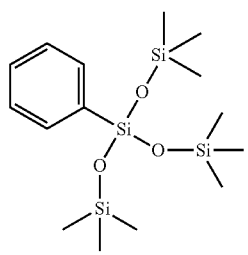

Phenyl-Tris(trimethylsiloxy)-silane

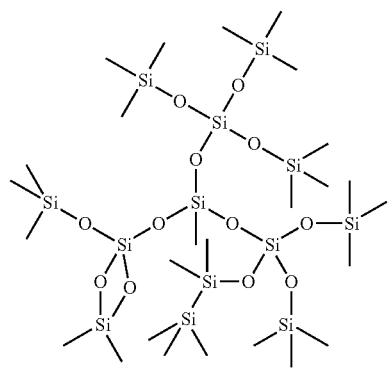

Tris[Tris(trimethylsiloxy)siloxy]methylsilane

Non-limiting examples of silane containing hydrophobic groups are polydimethylsiloxanes containing terminal tris (trimethylsiloxy)siloxy, Bis{3-[tris(trimethylsiloxy)silyl] propyl}fumarate, methyltris(trimethylsiloxy)silane, 3-acryloxypropyltris(trimethylsiloxy)silane, 3-methacryloxypropyltris(trimethylsiloxy)silane, p-styryltris(trimethylsiloxy)silane, 2-(5-norbornenyl)ethyltris(trimethylsiloxy)silane, tris(trimethylsiloxy)methoxysilane, tris(trimethylsiloxy)ethoxysilane, tris(trimethylsiloxy)silanol, tris(triethylsiloxy)methoxysilane, tris(triethylsiloxy)ethoxysilane, tris(triethylsiloxy)silanol, allyltris(trimethylsiloxy) silane, or allyltris(triethylsiloxy)silane.

The cross-linkers used in the materials of the present invention may cross link the polymers into a dense network and provide good mechanical properties. In a specific embodiment, the cross linkers are trimethoxysilylpropyl methacrylate (TMOSPMA), or 2-hydroxyethyl methacrylate (HEMA). The non-limiting examples of cross-linkers have structures V, VI, VII, VIII or IX.

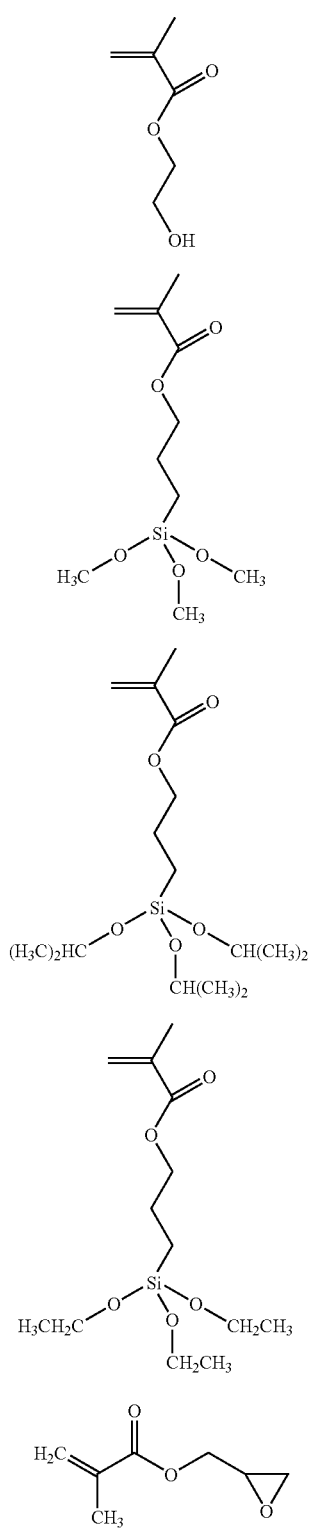

Some compositions of non bio-adhesive copolymers comprise at least one $M_3T$, at least one cross linker comprising a derivative of acrylate and at least one monomer of an acrylate or its derivative. In one embodiment, the appended TRIS groups present in $M_3T$ are hydrophobic in nature. In a further embodiment, the appended hydrophobic groups may be selected from the molecules containing silane moieties. In one example, the appended hydrophobic group may contain a non-silane moiety.

In one embodiment, the hydrophobic groups are parts of units of the polymeric materials, which applied on the surface of the device. Polymeric material may comprise silane containing monomer. In another embodiment, the polymeric material may comprise silane containing material and at least a cross-linker. A precursor for the coating polymer may comprise units of at least a first monomer that is hydrophobic and at least units of a second monomer that has a reactive functional group. In a specific embodiment, the first monomer unit is $M_3T$. The first monomer unit may be a silane functional group containing molecule. The second monomer may be hydrophobic or hydrophilic and may be a cross-linker, which cross-links polymer units to increase mechanical strength. The cross-linker may contain a reactive group. Non-limiting examples of the reactive group are siloxy, epoxy, —OH, —$NH_2$, —COOH, —$CONH_2$, —COCl, —COBr, —SH, —NH—, —NCO, unsaturated carbon-carbon groups or a combination thereof. For example, the second monomer unit may be trimethoxysilylpropyl methacrylate (TMOSPMA) or 2-hydroxyethyl methacrylate (HEMA) or glycidyl methacrylate (GMA). In other example, the second monomer unit may contain a functional group (R) wherein the functional group may be selected from any siloxy containing groups. There may be a third monomer unit, which is an acrylate or derivative of an acrylate. The third monomer unit may be an alkyl acrylate. In a non-limiting example, the third monomer unit may be methacrylate. In a specific embodiment, the third monomer unit is propyl methacrylate.

The non bio-adhesive copolymer composition may comprise $M_3T$ in a range from about 1 to 100 or from about 20 to 90 mole percent. In another embodiment, the non bio-adhesive copolymer composition may comprise one cross linker comprising a derivative of an acrylate in a range from about 0 to 30 mole percent. In yet another embodiment, the non bio-adhesive copolymer composition may comprise an acrylate derivative in a range from about 0 to 90 mole percent. The non bio-adhesive copolymer composition may comprise at least one hydrophobic moiety comprising $M_3T$, at least one cross linker comprising a derivative of acrylate, and at least a monomer of acrylate derivative in varying mole ratios of 10:0:0, 10:1:0, 8:1:2, 6:1:4, 4:1:6, 2:1:8, 1:1:9, 0.6:1:9.4, 0.2:1:9.8, 1:3:10, 2:3:8, 9.6:0.4:0, 9:1:0, 8:2:0, 7:3:0.

Some embodiments of the methods for making a device having a non bio-adhesive surface generally comprise the step of applying a material comprising a plurality of groups representing structure (I), to coat a surface of a substrate. The material may comprise polymers, oligomers, small molecules or organic-inorganic hybrids or a combination thereof. Multiple coating techniques may be used to coat the surface of a substrate, such as a medical device or cell based assay or culture systems. Such coating techniques include, but are not limited to, spraying, brushing, dip-coating, spin-coating, printing, sputtering, casting, physical vapor deposition, chemical vapor deposition, or plasma coating.

EXAMPLE 1

Synthesis of Tris-trimethylsilylpropyl Containing Acrylate Copolymer

Materials: White Spirit was purchased from Aldrich and all other solvents were purchased from Sinopharm Chemical Reagent Co., Ltd (China). Tris-trimethylsilylpropyl methacrylate ($M_3T$) and 3-aminopropyltrimethoxysilane (A1100) were obtained from GETOS (Japan) and GE silicones (China) respectively. Trimethoxysilylpropyl methacrylate (TMOSPMA), 2-hydroxyethyl methacrylate (HEMA), glycidyl methacrylate (GMA), dibutyltin dilaurate (DBTDL) and methylene diphenyl 4,4'-diisocyanate (MDI) were purchased from Aldrich. Polyisocyanate Desmodur N3300 was purchased from Bayer. Propyl methacrylate (PMA) was purchased from Alfa Aesar. The inhibitor remover, used to remove any inhibitor present in methacrylate monomers, was purchased from Aldrich. The initiator, 2,2'-azobis(2-methylpropionitrile) (AIBN), was purchased from Sinopharm Chemical Reagent Co., Ltd (China), and recrystallized from ethanol prior to its use.

Tris-trimethylsilylpropyl containing methacrylate ($M_3T$) copolymers were synthesized by solvent polymerization using AIBN as initiator. About 20.0 g (47.3 mmol) of $M_3T$, 1.17 g (4.7 mmol) of TMOSPMA, 1% AIBN (0.0854 g) and 110 mL toluene were added to a 250 mL two-neck round bottom flask and stirred with a magnetic stirrer. The mixture was degassed using freeze-pump-thaw cycles and Argon was introduced to the mixture to create an inert atmosphere. The temperature of the mixture was raised to room temperature, and then slowly the temperature was increased to 70° C., where the mixture was stirred for 48 hrs to form the desired copolymer. The copolymer was then dried and subsequently dissolved in White Spirit. The other two-component copolymers and three-component copolymers were synthesized by analogous procedures.

Synthesis of a Two-component Copolymers

A series of two-component copolymers tris-trimethylsilylpropyl methacrylate-co-trimethoxysilylpropyl methacrylate ($M_3T$-co-TMOSPMA) with different amounts of TMOSPMA (molar ratios of TMOSPMA to $M_3T$ were 0.4/10, 1/10, 2/10 and 3/10) were obtained by following the copolymer synthesis process described above. The structures of the copolymers ($M_3T$-co-TMOSPMA) were verified by $^1H$ NMR analysis and component analysis. The structures of the copolymer were determined by component analysis software calculations based on integrations of the assigned peaks.

Synthesis of a Three-component Copolymer

In order to improve the mechanical properties of the film such as hardness and to obtain a higher glass transition temperature (Tg), propyl methacrylate (PMA) was used to synthesize the copolymers. A three-component copolymer, tris-trimethylsilylpropyl methacrylate-co-trimethoxysilylpropyl methacrylate-co-prolyl methacrylate ($M_3T$-co-TMOSPMA-co-PMA), with the cross-linking functionality was synthesized following the same process as for the two component copolymers described above. Synthesis of copolymer $M_3T$-co-TMOSPMA-co-PMA is schematically described below (scheme 1).

Scheme 1

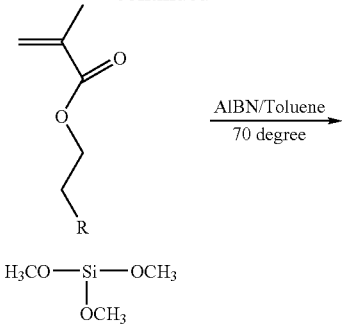

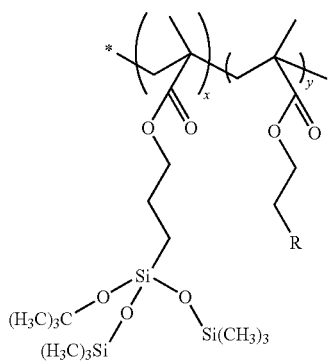

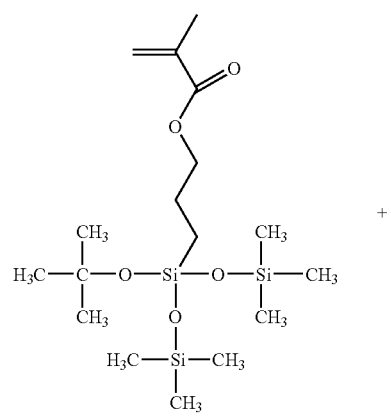

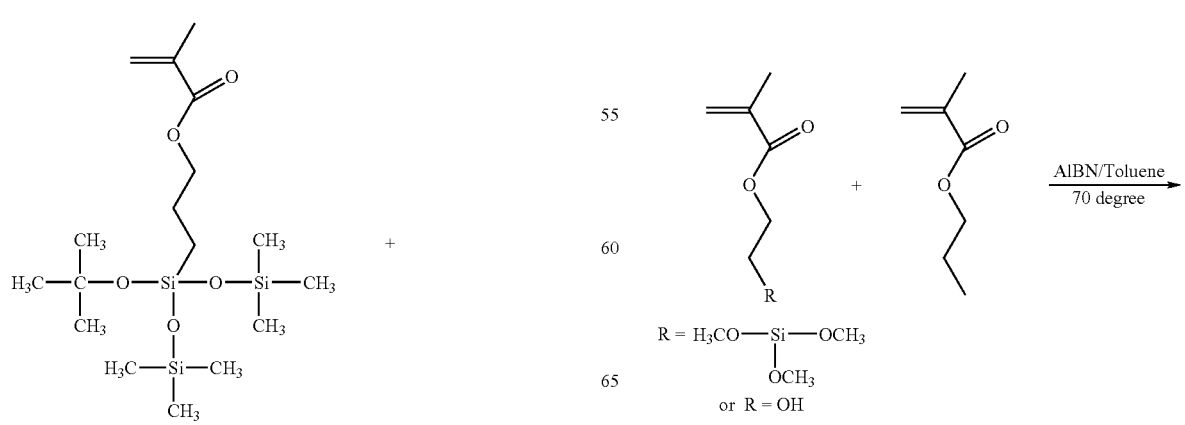

-continued

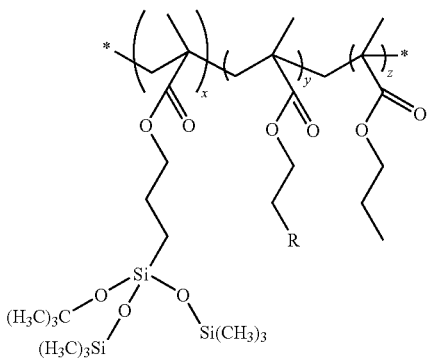

EXAMPLE 2

Formation of Coatings on Carbon Steel Panels

Several samples of carbon steel panels were washed with isopropanol and dried at room temperature. An anti-corrosive undercoat Safeguard Universal ES (from Jotun, Sandefjord, Norway) was applied to a carbon steel panel. Five parts of a base (pre-polymer) was mixed with one part of a curing agent using a high speed mixer and the mixture was then applied to the same carbon steel panel using a 300 μm draw-down bar, followed by overnight curing at room temperature. The panel thus prepared was stored in a sealed container. The synthesized copolymers were further concentrated to the required concentration (about 30% by weight) by rotary-evaporation, mixed with a catalyst and/or a curing agent (about 1 wt % of the pure copolymer), and applied as another undercoat on the carbon steel panel using a 300 μm draw-down bar and finally cured either keeping the panel at room temperature for 5 days or keeping at 80° C. for 4 hrs.

EXAMPLE 3

Synthesis and Characterization of $M_3T$-co-TMOSPMA Copolymer Film/Coating

In one example, the copolymer $M_3T$-co-TMOSPMA was mixed with DBTDL and A1100. The mixture was applied to the basecoat of a carbon steel panel using a 300 μm draw-down bar to form a film (or coating). The film was characterized using water contact angle measurements and pencil hardness tests, and the results are shown in Table 1. For this class of copolymers, the coatings formed on glass slides were transparent. The molar ratio of TMOSPMA to $M_3T$ and the curing temperature appear to have limited effect on the coating surface properties and mechanical properties.

TABLE 1

Characterization of different ($M_3T$-TMOSPMA) copolymer

| Polymer | Curing process | Water Contact Angle (°) | Pencil hardness |
|---|---|---|---|
| Coplymer($M_3T$-TMOSPMA) with molar ratio of 10/1 | Room temperature for 5 days | 99 +/− 0.4 (remove error, since it is higher than these numbers) | softer than 6B |
|  | 80° C. for 4 hrs | 98 +/− 0.3 | softer than 6B |
| Coplymer($M_3T$-TMOSPMA) with molar ratio of 10/2 | Room temperature for 5 days | 99 +/− 0.3 | softer than 6B |
|  | 80° C. for 4 hrs | 99 +/− 0.6 | About 6B |
| Coplymer($M_3T$-TMOSPMA) with molar ratio of 10/3 | Room temperature for 5 days | 100 +/− 0.7 | softer than 6B |
|  | 80° C. for 4 hrs | 101 +/− 0.4 | About 6B |

EXAMPLE 4

Figure 1B:
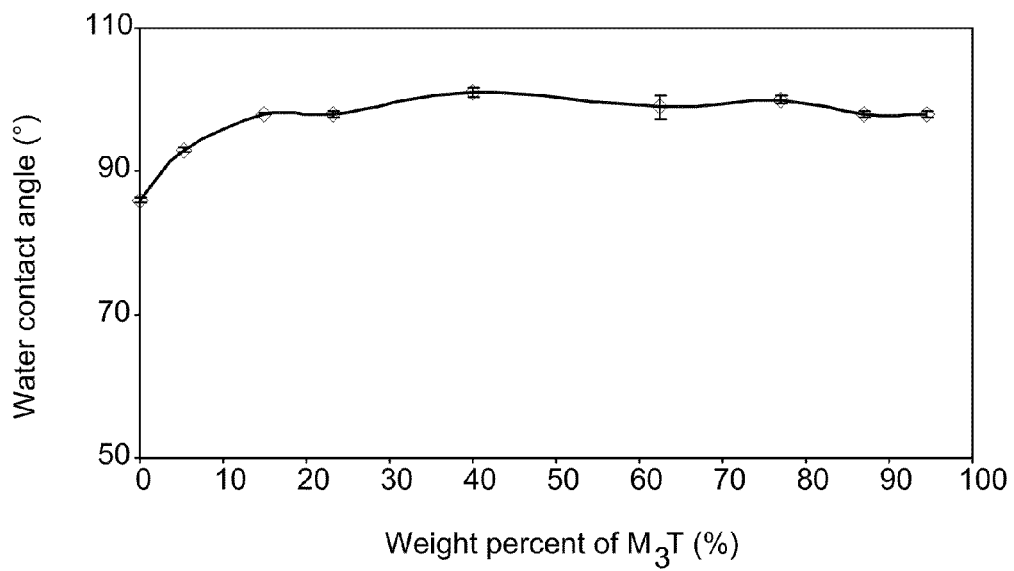
FIG. 1B is a graph showing the dependence of water contact angle with weight percent of $M_3T$.

Synthesis and Characterization of $M_3T$-co-TMOSPMA-co-PMA Copolymer Film/Coating In another example, the copolymer $M_3T$-co-TMOSPMA-co-PMA was mixed with DBTDL and A1100. The mixture was applied to the basecoat of a carbon steel panel sample to form films (or coating) using a 300 μm draw-down bar. The films having different amounts of PMA were characterized using water contact angle measurements and pencil hardness tests, and the results are shown in Table 2. The results in FIGS. 1A and 1B, show that when the $M_3T$ mole percent was more than 6% or the $M_3T$ weight percent was more than 15%, the change in the measured contact angle for water on the film was found to be less compared to the change in said angle when $M_3T$ mole percent and weight percent was less than 6% or 15% respectively. When the $M_3T$ mole percent was less than 6% or the $M_3T$ weight percent was less than 15%, the contact angle for water increased with increased amounts of $M_3T$. Without $M_3T$, the water contact angle was only 86 degrees.

TABLE 2

Characterization of different compositions of ($M_3$T-PMA-TMOSPMA) copolymer

| Polymer | $M_3$T mol % | $M_3$T wt % | Water Contact Angle (°) | Pencil hardness |
|---|---|---|---|---|
| $M_3$T/PMA/TMOSPMA = 10/0/1 | 91 | 94 | 98 +/− 0.5 | softer than 6B |
| $M_3$T/PMA/TMOSPMA = 8/2/1 | 73 | 87 | 98 +/− 0.5 | softer than 6B |
| $M_3$T/PMA/TMOSPMA = 6/4/1 | 55 | 77 | 100 +/− 0.6 | softer than 6B |
| $M_3$T/PMA/TMOSPMA = 4/6/1 | 36 | 62 | 99 +/− 1.6 | About 6B |
| $M_3$T/PMA/TMOSPMA = 2/8/1 | 18 | 40 | 101 +/− 0.7 | About 6B |
| $M_3$T/PMA/TMOSPMA = 1/9/1 | 9 | 23 | 98 +/− 0.4 | About 6B |
| $M_3$T/PMA/TMOSPMA = 0.6/9.4/1 | 5 | 15 | 98 +/− 0.1 | About 6B |
| $M_3$T/PMA/TMOSPMA = 0.2/9.8/1 | 2 | 5 | 93 +/− 0.3 | About 6B |
| $M_3$T/PMA/TMOSPMA = 0/10/1 | 0 | 0 | 86 +/− 0.4 | B |

EXAMPLE 5

Synthesis and Characterization of a Copolymer ($M_3$T-co-TMOSPMA-co-PMA) Film/Coating with Improved Hydrophobicity and Mechanical Property Three component copolymers $M_3$T-co-TMOSPMA-co-PMA were synthesized by varying the number of curing groups. The molar ratios of the materials synthesized as well as their measured properties are shown in Table 3. When the molar ratio of $M_3$T to PMA was fixed at 2/8 and the amount of curing group TMOSPMA was increased from 10 mol % to 30 mol %, the water contact angle measured on the film changed little, but the pencil hardness showed significant improvement, going from 6B to B. These results suggest that increasing the molar content of the curing group may be an effective way to improve the coating hardness.

EXAMPLE 6

Synthesis of Three Component Copolymers and Determination of Water Contact Angle and Pencil Hardness A series of $M_3$T containing copolymers were synthesized and certain surface and mechanical properties of copolymer coatings were characterized. The effect of the amount of curing group TMOSPMA and hard component PMA used for synthesizing copolymer were analyzed. Use of more curing group and harder component resulted in better mechanical property. The three-component copolymer $M_3$T-co-TMOSPMA-co-PMA with a molar ratio of 2:1:8 is one example formulation that formed a hydrophobic coating with good mechanical properties with respect to B hardness.

TABLE 3

Determination of water contact angle and pencil hardness

| Polymer | Water Contact Angle (°) | Pencil hardness |
|---|---|---|
| M3T:PMA:TMOSPMA = 2:8:1 | 101 +/− 0.7 | About 6B |
| M3T:PMA:TMOSPMA = 2:8:3 | 98 +/− 0.4 | B |
| M3T:PMA:TMOSPMA = 0:10:1 | 86 +/− 0.4 | B |
| M3T:PMA:TMOSPMA = 0:10:3 | 88 +/− 2.4 | HB |

The structures of the copolymers were examined using a Bruker Avance 400 MHz NMR spectrometer. NMR Spectra was used to analyze the components of the copolymers. The contact angles of water present on the coatings were measured by an OCA 20 instrument (DataPhysics). The coating hardness was tested by the pencil hardness tester (PPH-1, 1000 g, Shanghai Xiandai Environment Engineering Technique Co., Ltd) using standard procedures.

EXAMPLE 7

Bacterial Cell Adhesion

Figure 2A:
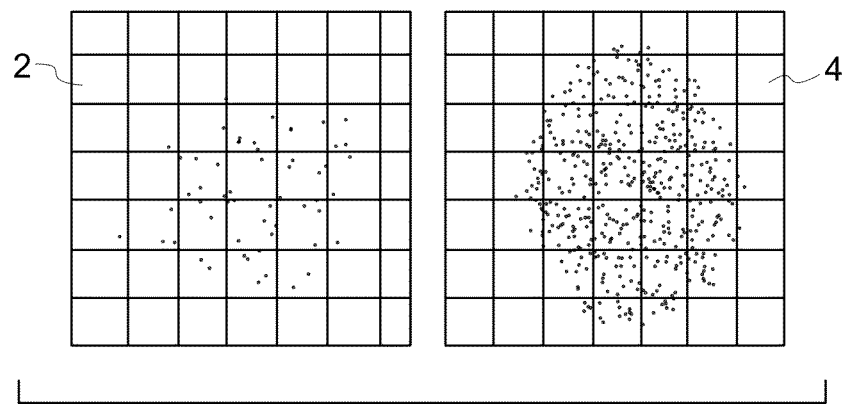
FIG. 2A is an image of bacterial suspensions, derived from uncoated stainless steel surfaces, inoculated on 3M™ Petrifilm™ at dilutions of 1:1000 (2) and 1:100 (4).
Figure 2B:
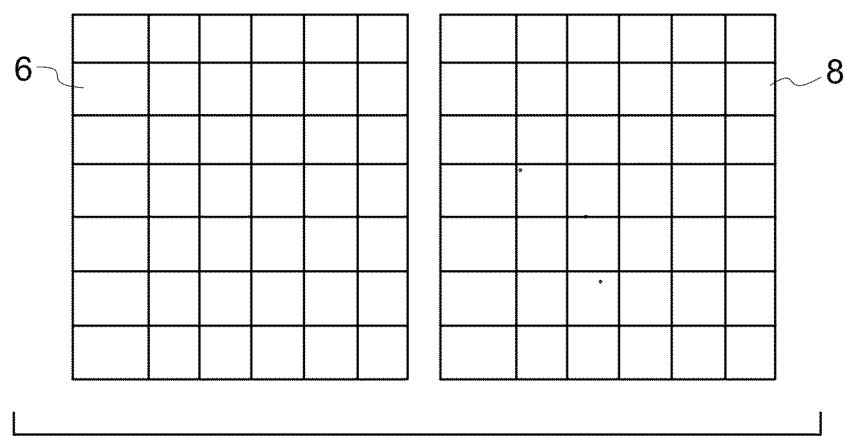
FIG. 2B is an image of bacterial suspensions, derived from stainless steel surfaces with coating of the present invention, inoculated on 3M™ Petrifilm™ at dilutions of 1:10000 (6) and 1:1000 (8).

In one example, bacterial cell adhesion on an uncoated surface and on a coated surface of stainless steel was examined. Bacterial cells, *Pseudomonas fluorescens* (from ATCC) were grown on stainless steel surface with coating of copolymer $M_3$T-co-TMOSPMA-co-PMA and on uncoated stainless steel surface. The bacterial cells grown on uncoated or on coated surface were taken and diluted to different suspensions. The suspensions from uncoated surface were then inoculated on 3M™ Petrifilm™ coupons (FIG. 2A) at dilutions of 1:1000 (2) and 1:100 (4). The suspensions from coated surface were then inoculated on 3M™ Petrifilm™ coupons (FIG. 2B) at dilutions of 1:10000 (6) and 1:1000 (8). Bacterial cells, *Pseudomonas fluorescens* (from ATCC) were grown on 316SS uncoated surface (8.77 cm each) and 316SS coated stainless steel surface (6 cm² each) at 30° C. for 24hrs. Cells were removed from the uncoated and coated stainless steel surfaces and were suspended in 35 ml of 0.85% phosphate buffered saline. Bacterial suspensions in different dilutions were made and inoculate onto 3M™ Petrifilm™ Plates (coupons), followed by incubation at 30° C. for 48hrs. The bacterial suspensions were added on to the uncoated coupon in a 1:10000 dilution (FIG. 2A, element 2) and in a 1:1000 dilution (FIG. 2A, element 4). The bacterial suspension was added on to the coated coupons in a 1:1000 dilution (FIG. 2B, element 6) and in a 1:100 dilution (FIG. 2B, element 8). Bacterial colonies attached on to the coupons were counted by 3M™ Petrifilm™ Plate Reader and the total number of colonies for each bacterial sample in different dilutions were calculated (shown in Table 4). Colony count for bacteria attached to the coated coupons is at least 150 times less than colony count for bacteria attached to 316 SS uncoated coupons, as shown in FIGS. 2A and 2B.

TABLE 4

Colony count for bacteria attached to the uncoated or coated coupons

| Attached Coupons | | Dilution | cfu/test ml | cfu/cm² |
|---|---|---|---|---|
| 316SS uncoated coupons | Coupon 1 | 1/1000 | 500,000 | 1,995,439 |
| | Coupon 2 | | 500,000 | 1,995,439 |
| | Coupon 3 | | 510,000 | 2,035,348 |
| Coated coupons | Coupon 1 | 1/1000 | 300 | 1,750 |
| | Coupon 2 | | 2,200 | 12,833 |
| | Coupon 3 | | <100 | / |
| | Coupon 4 | | <100 | / |

EXAMPLE 8

Mammalian Cell Adhesion

Mammalian cell adhesion was examined for uncoated and coated surfaces. Chinese Hamster Ovary (CHO-K1) cells and human breast cancer cells (MDA-MB-231) were purchased from ATCC. The culture media used for growing cells was Leibovitz's L-15 and was purchased from ATCC. Cells were seeded and cultured on to coated and uncoated glass slides and on coated and uncoated polystyrene Petri dishes.

Figure 3A:
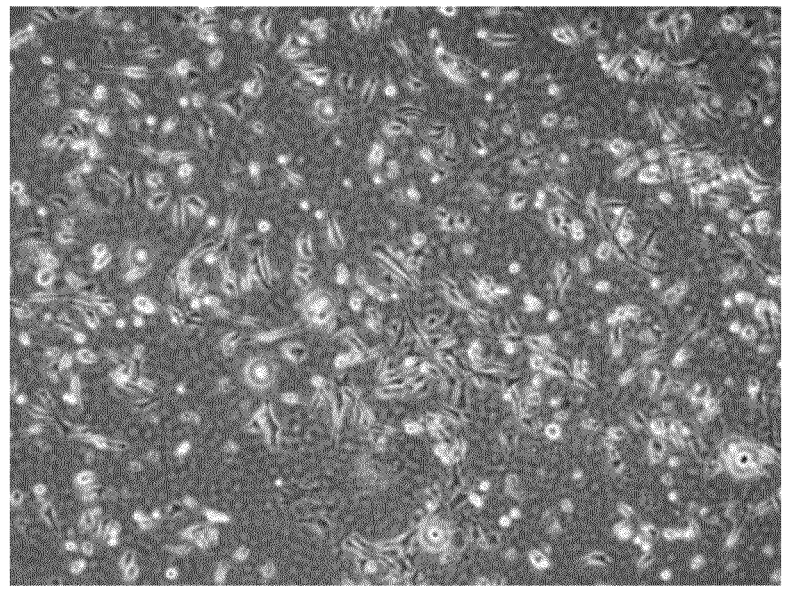
FIG. 3A is an image of mammalian cells grown on an uncoated glass slide.
Figure 3B:
FIG. 3B is an image of mammalian cells grown on a surface of a glass slide with a coating of the present invention.

The copolymer $M_3T$-co-TMOSPMA-co-PMA was applied as a coating on a surface of a glass slide, and then cured at room temperature for overnight followed by incubation at 80° C. for 1 day. Uncoated and coated glass slides were placed into mammalian cell culture plates (having diameter of 6 cm). Suspended CHO-K1 cells were added on to each plate, and the plates were incubated at 37° C., in the presence of 5% $CO_2$ for 48 hrs in a $CO_2$ incubator. The slides were observed under Phase Contrast Microscope and the microscopy images clearly distinguish the uncoated and coated slides with respect to cell growth (FIGS. 3A and 3B).

Figure 4:
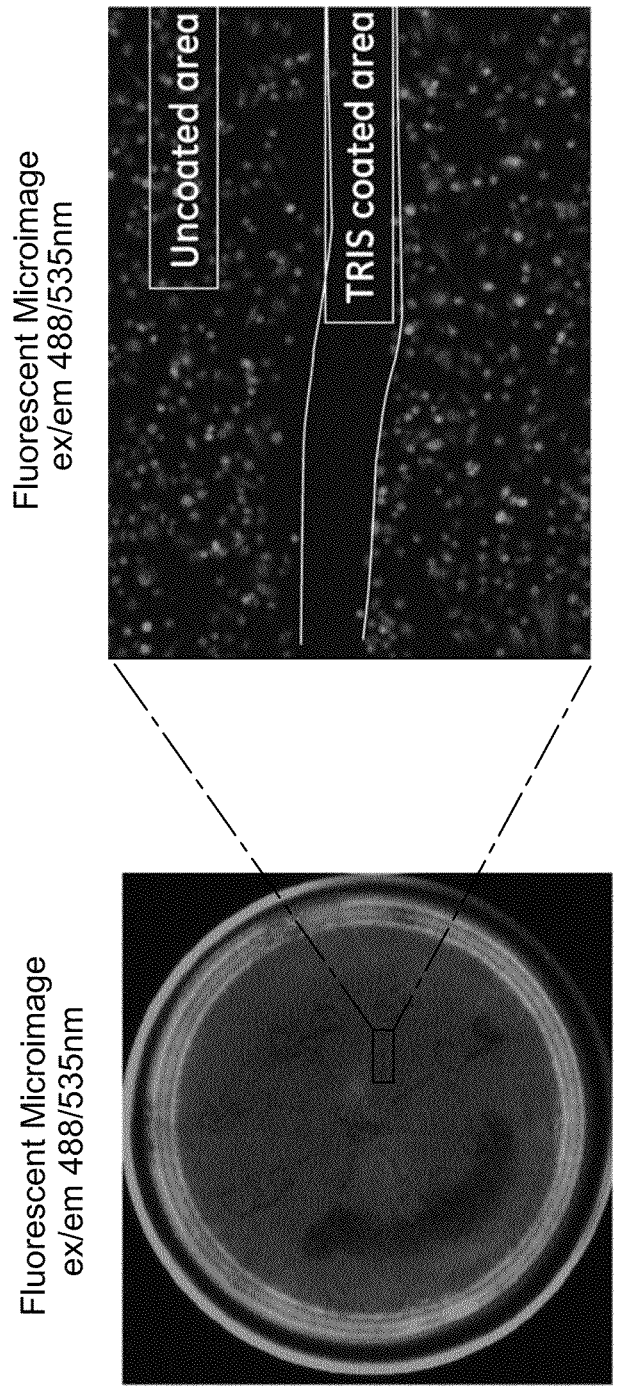
FIG. 4 is a micro-image of a polystyrene dish with an example of a surface coating of the invention treated with human breast cancer cells.
Figure 5:
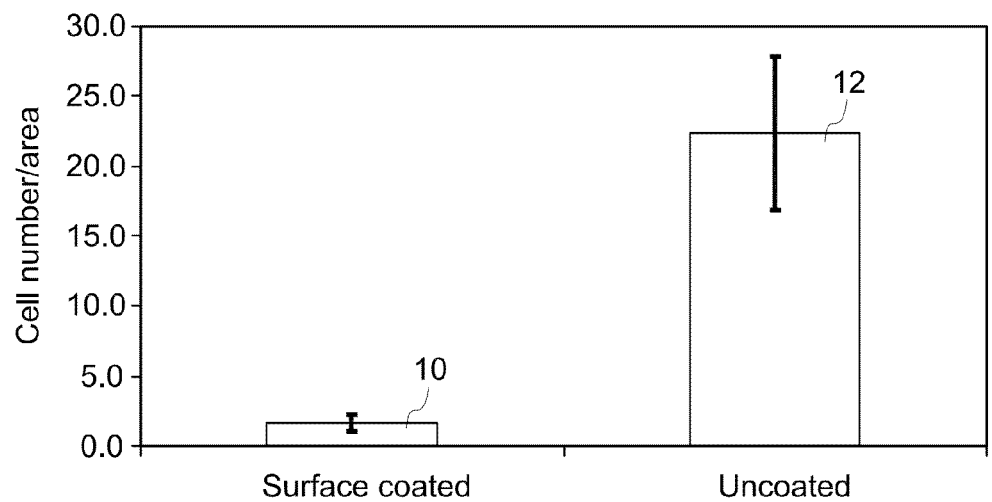
FIG. 5 is bar graphs illustrating variation in cell growth numbers for an uncoated area of a polystyrene dish (12) treated with human breast cancer cells and on an area of the polystyrene dish with a surface coating of the present invention (10) treated with human breast cancer cells.

The copolymer $M_3T$-co-TMOSPMA-co-PMA was applied as a coating on a portion of a surface of a polystyrene Petri dish (having diameter of 35 mm) to make a selectively coated surface. This selectively surface coated Petri dish was used to test cell growth on the coated and on the uncoated area. Human breast cancer cells (MDA-MB-231) were seeded on to the surface of the polystyrene Petri dish and incubated at 37° C. for 2 hrs. The cells were stained with CellTracker™ Green CMFDA (5-chloromethylfluorescein diacetate). After 2 hrs of growth, the dishes were rinsed briefly by phosphate buffered saline (PBS) followed by taking a microimage at 4× magnification and a macroimage by using a fluorescence plate scanner at Excitation/Emission at 488 nm/535 nm, as shown in FIG. 4. CellTracker™ reagents are fluorescent chloromethyl derivatives that freely diffuse through the membranes of live cells. Once inside the cell, these mildly thiol-reactive probes react with intracellular components. Therefore, the cells produced from the parent cells are both fluorescent and viable for at least 24 hrs after loading of this reagent. CellTracker™ Green CMFDA has a relatively low pKa, which ensures that it will exhibit bright, green fluorescence in the cytoplasm at all physiological pH levels. Fluorescence image (FIG. 4) show cell growth on uncoated area and clear, growth-less portions for $M_3T$-co-TMOSPMA-co-PMA copolymer coated area. Quantitative analysis of cell count data shows that the number of cells on the uncoated area (FIG. 5, bar 12) is 22.3±5.5/cm² and the number of cells on the coated area (FIG. 5, bar 10) is 1.7±0.6/cm², which is lower by over a factor of 10 as compared to the uncoated area. In an exemplary embodiment, the non bioadhesive copolymer composition comprises at least one hydrophobic moiety comprising tris(trimethylsiloxy)silyl, at least one cross linker comprising a derivative of methacrylate, and at least one monomer of methacrylate derivative in a ratio of 8:1:2. Ratio with high amount of M3T showed better cell repellent property.

EXAMPLE 9

Effect of Surface Tension on Coating Property

Figure 6:
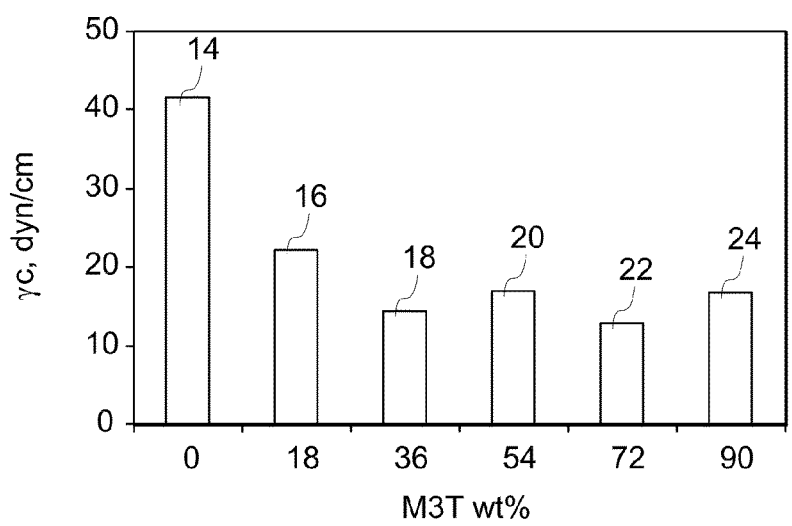
FIG. 6 represents a series of bar graphs illustrating the variation in measured critical surface tension of copolymer $M_3T$-co-TMOSPMA-co-PMA with varying concentrations of $M_3T$ (weight percentage).

In a polymer system, surface energy may reflect surface chemistry of a system or a device. Understanding surface chemistry and surface property may be revealed by studying the effect of surface energy on performance. In one example, to obtain a series of copolymers with different surface energies, the ratio of $M_3T$ to TMOSPMA was varied in a wide range. A terpolymer (three-component copolymer) system was designed to restore the surface property of the copolymer. By fixing the feed ratio of TMOSPMA to 10 mol % and varying the $M_3T$/PMA ratio, a series of terpolymers with different surface energies were synthesized. The critical surface tension of a coating varies with different $M_3T$ concentrations. FIG. 6 represents a series of bar graphs (bars 14-24) illustrating the variation of critical surface tension for copolymer $M_3T$-co-TMOSPMA-co-PMA coatings with varying concentrations of $M_3T$ (weight percentage), while the concentration of TMOSPMA remained fixed. It can be seen from FIG. 6 that the critical surface tension decreases initially with increased concentrations of $M_3T$, and then levels off as $M_3T$ is further increased to saturate the $M_3T$ distribution on the coating surface.

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:

1. A device comprising:

a substrate; and a copolymer comprising:

a plurality of Structure (I) groups:

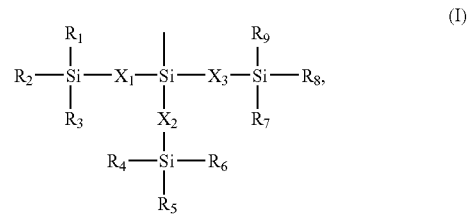

wherein $R_1$, $R_2$, $R_3$, $R_4$, $R_5$, $R_6$, $R_7$, $R_8$ and $R_9$ are independently at each occurance a C1-C10 aliphatic radical, a C3-C20 cycloaliphatic radical, or C6-C20 aromatic radical; and $X_1$, $X_3$ are independently at each occurance a sulphur, nitrogen, oxygen, or carbon, and $X_2$ is independently at each occurance a sulphur, nitrogen, or oxygen;

at least one cross linker comprising a derivative of an acrylate; and at least one monomer of an acrylate or its derivative, wherein the material is provided on at least a portion of the substrate, and has an exposed surface that is non-bioadhesive.

2. The device of claim 1, wherein the material comprises a plurality of Tris(trimethylsiloxy)silyl groups.

3. The device of claim 2, wherein the Tris(trimethylsiloxy) silyl groups are hydrophobic.

4. The device of claim 1, wherein the substrate comprises a microarray plate, a culture plate, a cell based assay system, a slide, a membrane, a vessel, a tank, or at least a portion of a medical device.

5. The device of claim 4, wherein the substrate comprises a material selected from glass, ceramic, polymer, steel or a combination thereof.

6. A non bio-adhesive copolymer composition comprising: at least one Structure (I) groups,

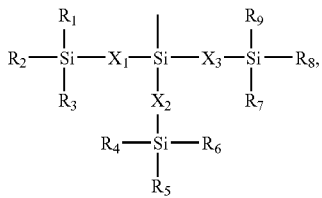

(I)

wherein $R_1$, $R_2$, $R_3$, $R_4$, $R_5$, $R_6$, $R_7$, $R_8$ and $R_9$ are independently at each occurance a C1-C10 aliphatic radical, a C3-C20 cycloaliphatic radical, or C6-C20 aromatic radical; and $X_1$, $X_3$ are independently at each occurance a sulphur, nitrogen, oxygen, or carbon, and $X_2$ is independently at each occurance a sulphur, nitrogen, or oxygen;
at least one cross linker comprising a derivative of an acrylate; and
at least one monomer of an acrylate or its derivative.

7. The non bio-adhesive copolymer composition of claim 6, wherein structure (I) group is a tris(trimethylsiloxy)silyl group.

8. The non bio-adhesive copolymer composition of claim 7, wherein the mole percent of the tris(trimethylsiloxy)silyl is in a range from about 1 to 100.

9. The non bio-adhesive copolymer composition of claim 7, wherein the mole percent of the tris(trimethylsiloxy)silyl is in a range from about 20 to 90.

10. The non bio-adhesive copolymer composition of claim 6, wherein the mole percent of the cross linker comprising a derivative of an acrylate is in a range from about 0 to 30.

11. The non bio-adhesive copolymer composition of claim 6, wherein the mole percent of the monomer of an acrylate or its derivative is in a range from about 0 to 90.

12. The non bio-adhesive copolymer composition of claim 6, wherein the composition comprises at least one hydrophobic moiety comprising tris(trimethylsiloxy)silyl, at least one cross linker comprising a derivative of methacrylate, and at least one monomer of methacrylate derivative in a ratio of 8:1:2.

* * * * *